(12) United States Patent
Tunc

(10) Patent No.: US 6,206,883 B1
(45) Date of Patent: Mar. 27, 2001

(54) BIOABSORBABLE MATERIALS AND MEDICAL DEVICES MADE THEREFROM

(75) Inventor: Deger C. Tunc, East Brunswick, NJ (US)

(73) Assignee: Stryker Technologies Corporation, Kalamazoo, MI (US)

( * ) Notice: Subject to any disclaimer, the term of this patent is extended or adjusted under 35 U.S.C. 154(b) by 0 days.

(21) Appl. No.: 09/263,268

(22) Filed: Mar. 5, 1999

(51) Int. Cl.⁷ .................................................. A61B 17/58

(52) U.S. Cl. ................................ 606/77; 606/69; 606/73; 606/154; 623/23.75; 528/354

(58) Field of Search ........................... 606/69, 70, 71, 606/72, 73, 75, 76, 77, 151, 154; 623/11, 23.75; 528/354, 355; 525/413, 415, 419, 420

(56) References Cited

U.S. PATENT DOCUMENTS

| | | | |
|---|---|---|---|
| 3,248,463 | 4/1966 | Wiley et al. | 264/95 |
| 3,531,561 | 9/1970 | Trehu | 264/210 |
| 3,636,956 | 1/1972 | Schneider | 128/335.5 |
| 3,739,773 | 6/1973 | Schmitt et al. | 128/92 |
| 3,797,499 | 3/1974 | Schneider | 128/334 R |
| 4,074,713 | 2/1978 | Capozza | 128/92 C |
| 4,263,185 | 4/1981 | Belykh et al. | 260/17.4 R |

(List continued on next page.)

FOREIGN PATENT DOCUMENTS

| | | |
|---|---|---|
| 42 26 465 | 2/1993 | (DE) . |
| 0202090 B1 | 11/1986 | (EP) . |
| 0299004 B1 | 1/1989 | (EP) . |
| 0321176 A3 | 6/1989 | (EP) . |
| 0321176 B! | 6/1989 | (EP) . |
| 0349656 A1 | 1/1990 | (EP) . |
| 0 401 844 | 12/1990 | (EP) . |
| 0 460 439 A2 | 12/1991 | (EP) . |
| 80 02641 | 12/1980 | (WO) . |
| 89 01767 | 3/1989 | (WO) . |
| 90 04982 | 5/1990 | (WO) . |
| 92 15342 | 9/1992 | (WO) . |
| 95 26762 | 10/1995 | (WO) . |
| WO 97 36553 | 10/1997 | (WO) . |

OTHER PUBLICATIONS

"Biodegradable materials of poly(L–lactic acid): 1. Melt–spun and solution–spun fibres," Eling et. al, (6 pages) (1992).

"Bioreabsorbable Plastic Materials for Bone Surgery", Vert, et. al, Maromolecular Biomaterials, pp. 119–141.

"Copolyester Studies, III. Melt–Spinning, Drawing, and Mechanical Properties of Tetramethylene Terephthalate–Tetramethylene Sebacate Copolymer Fibers", Marrs, et. al, Journal of Applied Polymer Science, vol. 23, pp. 1095–1104 (1979).

"Elastic Moduli of Highly Oriented Polyoxymetheylene", Choy, et al, Polymer Engineering and Science, vol. 23, No. 16, pp. 910–922, (1983).

"Enhancement of the mechanical properties of polylactides by solid–state extrusion", Weiler, et. al, Biomaterials, vol. 17, No. 5 pp. 529–535 (1996).

(List continued on next page.)

Primary Examiner—Michael Buiz
Assistant Examiner—David O. Reip
(74) Attorney, Agent, or Firm—Lerner, David, Littenberg, Krumholz & Mentlik, LLP

(57) ABSTRACT

A bioabsorbable material such as a terpolymer of poly-(L-lactide/D-lactide/glycolide). The material may consist of 85 molar percent L-lactide, 5 molar percent D-lactide, and 10 molar percent glycolide. The material may have a heat of fusion of about 15–25 J/G, tensile strength retention at 26 weeks of incubation of at least about 50%, and tensile strength retention at 52 weeks of incubation of at most about 25%. The material may be used in implantable devices such as bone fixation devices.

31 Claims, 15 Drawing Sheets

U.S. PATENT DOCUMENTS

| | | | |
|---|---|---|---|
| 4,523,591 | 6/1985 | Kaplan et al. | 128/334 R |
| 4,539,981 | 9/1985 | Tunc | 128/92 B |
| 4,550,449 | 11/1985 | Tunc | 623/16 |
| 4,640,271 | 2/1987 | Lower | 128/92 YF |
| 4,655,771 | 4/1987 | Wallsten | 623/1 |
| 4,655,777 | 4/1987 | Dunn et al. | 623/16 |
| 4,671,280 | 6/1987 | Dorband et al. | 128/334 C |
| 4,743,257 | 5/1988 | Törmälä et al. | 623/16 |
| 4,781,183 | 11/1988 | Casey et al. | 128/92 YP |
| 4,898,186 | 2/1990 | Ikada et al. | 606/62 |
| 4,905,680 | 3/1990 | Tunc | 606/69 |
| 4,924,865 * | 5/1990 | Bays et al. | 606/77 |
| 4,968,317 | 11/1990 | Törmälä et al. | 606/77 |
| 5,084,050 | 1/1992 | Draenert | 606/77 |
| 5,201,738 | 4/1993 | Scott et al. | 606/77 |
| 5,319,038 | 6/1994 | Tunc | 525/415 |
| 5,569,250 | 10/1996 | Sarver et al. | 606/69 |
| 5,747,390 | 5/1998 | Cooper et al. | 442/59 |
| 5,747,637 | 5/1998 | Shinoda et al. | 528/354 |
| 5,824,247 | 10/1998 | Tunc | 264/135 |
| 5,827,287 | 10/1998 | Tunc | 606/76 |

OTHER PUBLICATIONS

"Resorbable Materials of Poly(L–Lactide). II Fibers Spun from Solutons of Poly (L–Lactide) in Good Solvents", Gogolewski et al., Journal of Applied Polymer Science, vol. 28, pp. 1045–1061 (1983).

"Standard Test Method for Tensile Properties of Plastics", 1994 ASTM Annual Book of ASTM Standards, vol. 08.01, Plastics (I): D638 and D638M–93, pp. 47–67 (1995).

Kirk P. Andriano et al., "Processing and Characterization of Absorbable Polylactide Polymers for Use in Surgical Implants", *Journal of Applied Biomaterials*, vol. 5, pp. 133–140 (1994).

R. Ewers, M.D. et al., "Bioabsorbable Osteosynthesis Materials", Clinic for Maxillofacial and Plastic Face–Surgery, University of Vienna, Vienna, Austria, pp. 206–214 (1990).

"Poly (L–Lactide) for Use as Internal Fixation Material" —biocompatibility and preparation—. Chapter 2, PhD. Thesis, pp. 7–16 (pre 1990).

* cited by examiner

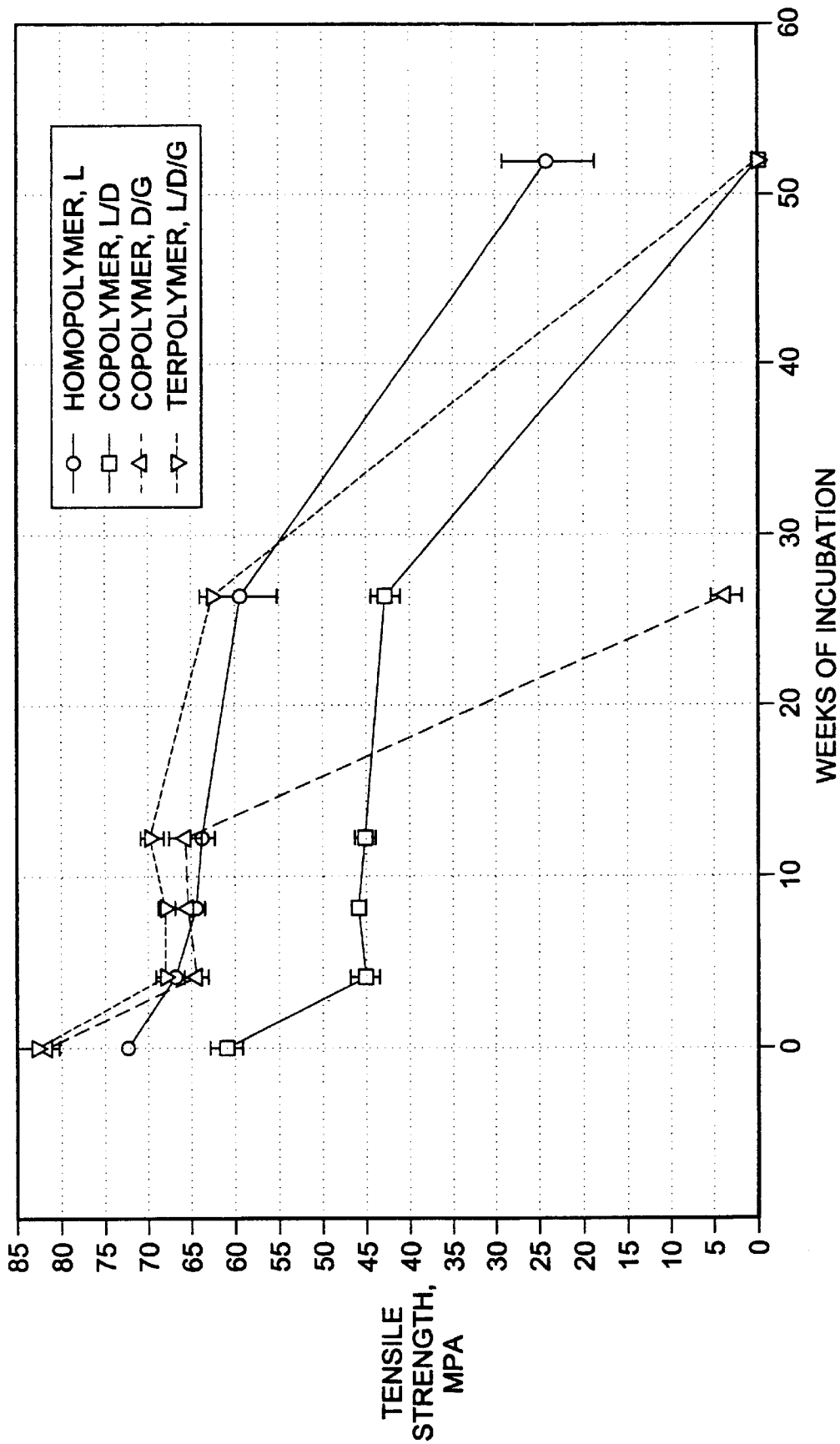
FIG-1 TENSILE STRENGTH AS A FUNCTION OF INCUBATION TIME AT PH 7.4, 37 C.

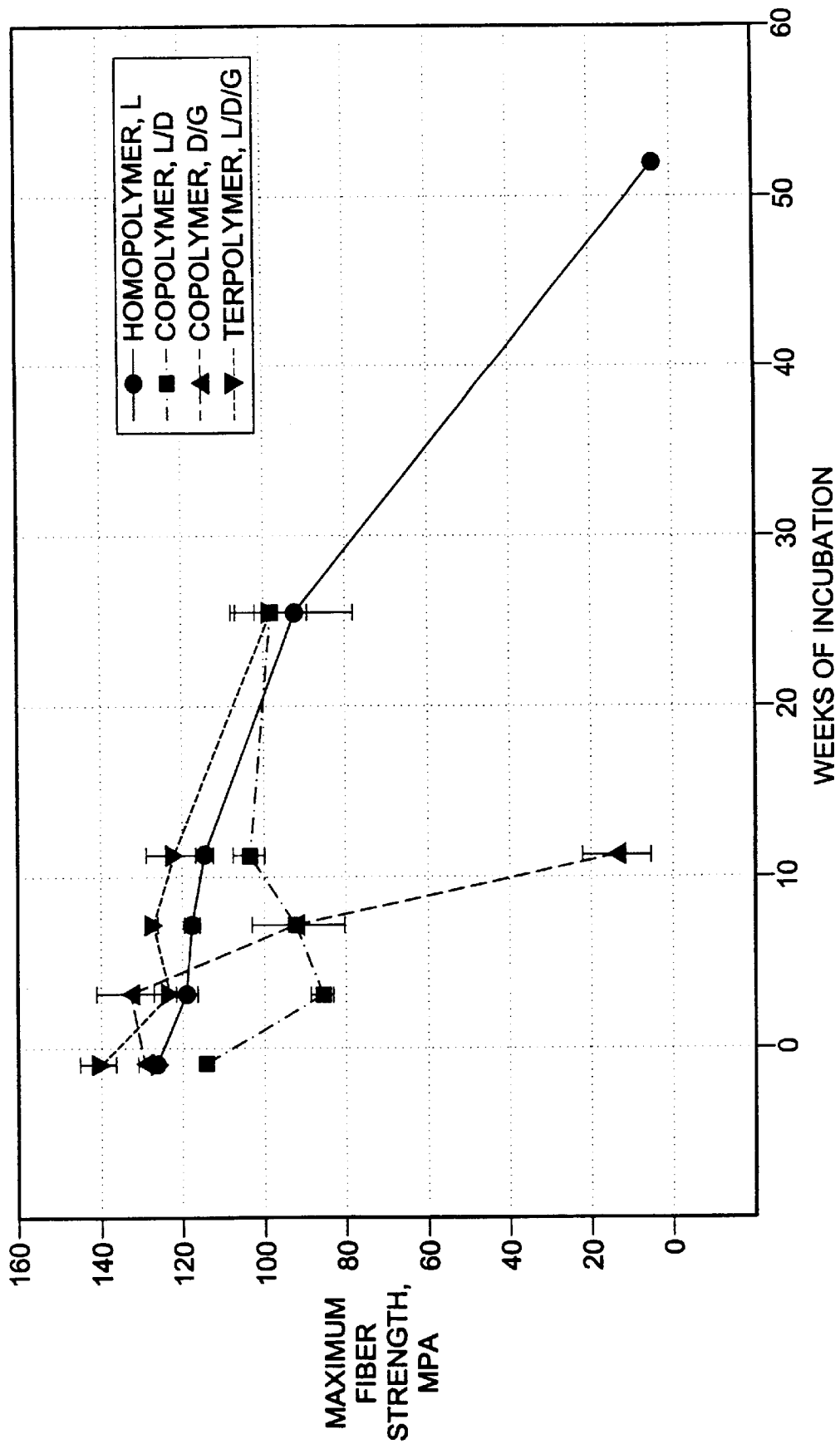

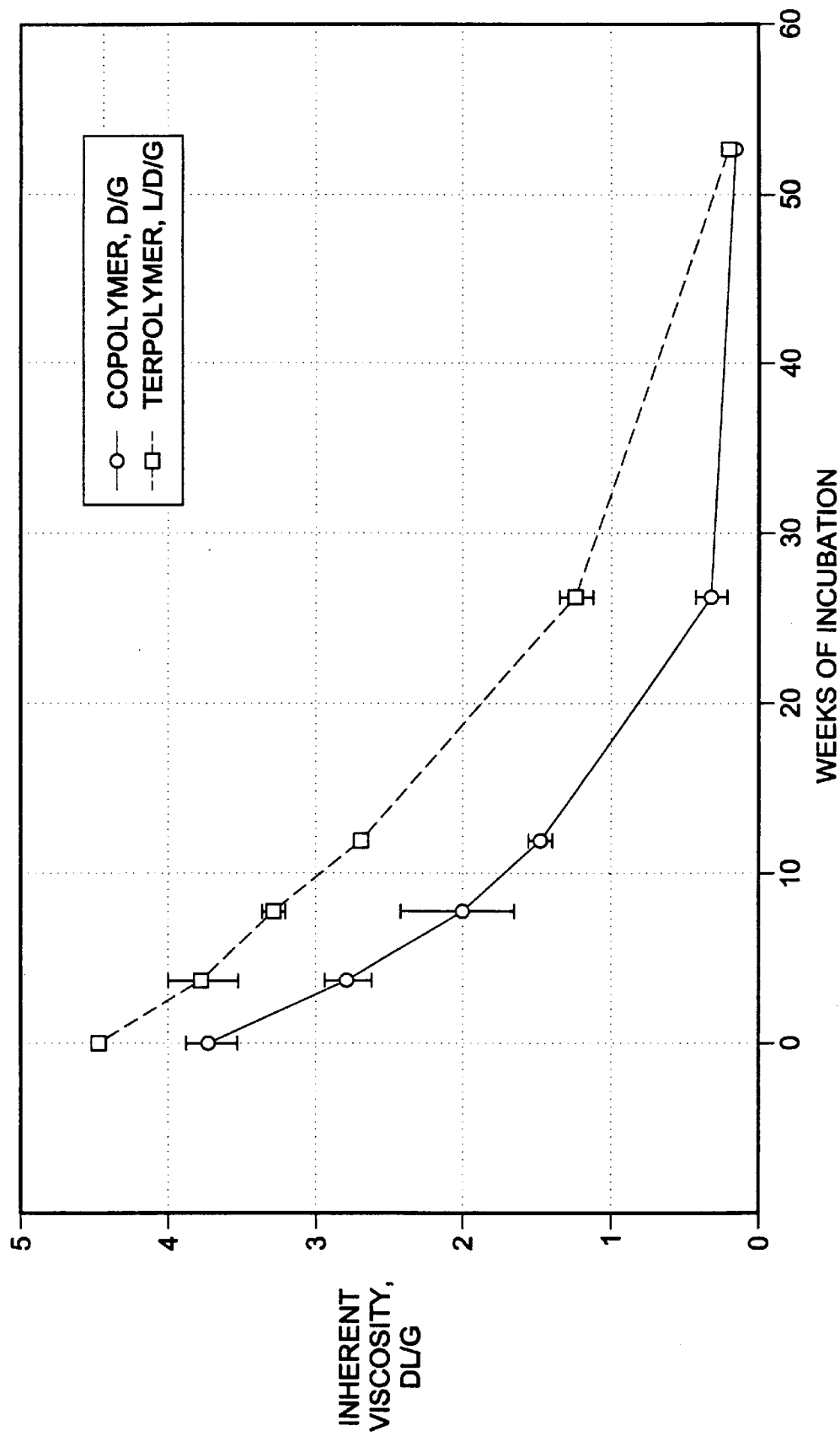
FIG-3 INHERENT VISCOSITY AS A FUNCTION OF INCUBATION TIME AT PH 7.4, 37 C.

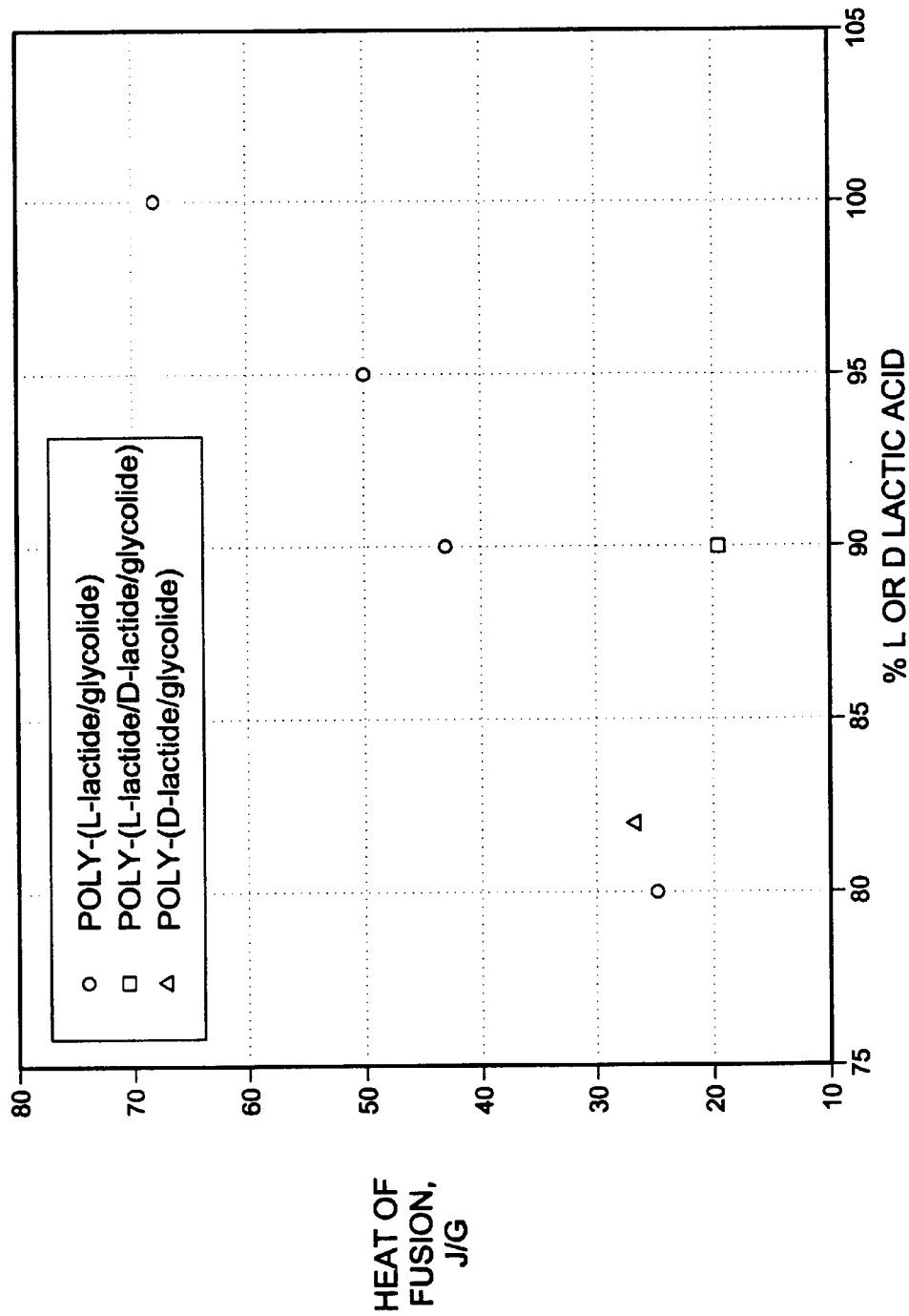
FIG-4 EFFECT OF THE POLYMER COMPOSITION ON THE HEAT OF FUSION OF THE POLYMERS

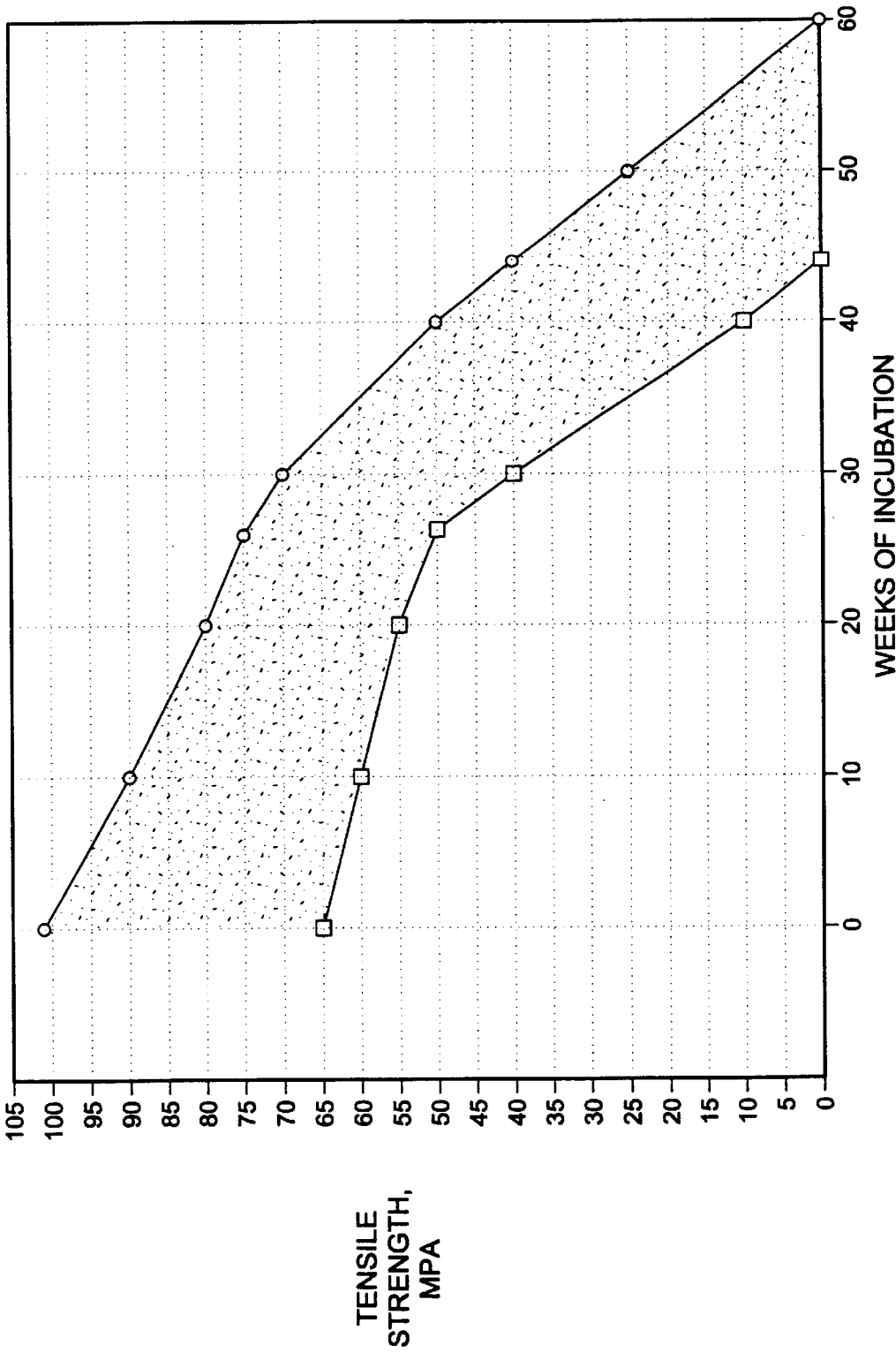
FIG-5 TENSILE STRENGTH AS A FUNCTION OF INCUBATION TIME AT PH 7.4, 37 C.

BIOABSORBABLE MATERIALS AND MEDICAL DEVICES MADE THEREFROM

FIELD OF THE INVENTION

This invention relates to bioabsorbable materials such as a terpolymer of poly-(L-lactide/D-lactide/glycolide), methods of making and using such materials, and to medical devices made from such materials.

BACKGROUND OF THE INVENTION

Commercially available bone fixation devices are often made of metal alloys which must be surgically removed after bone healing. The removal of such devices causes additional trauma to the patient as well as increased medical costs. Metallic devices also have moduli of elasticity which are 10–20 times higher than that of cortical bone, thus preventing the loading of the bone and possibly causing osteopenia due to stress shielding.

U.S. Pat. Nos. 4,539,981 and 4,550,449 to Tunc (the inventor of the present invention) relate to absorbable bone fixation devices made from high molecular weight polymer of L-lactide. However, such fixation devices have a relatively low rate of absorption and retain relatively high tensile strength after the bone fully heals.

U.S. Pat. No. 5,569,250 to Sarver et al. relates to a biocompatible osteosynthesis plate for securing a plurality of adjacent bone portions. It purportedly discloses, inter alia, non-reinforced lactide and glycolide copolymer (see, e.g., col. 6, lines 63 et seq.). However, such materials exhibit relatively low tensile strengths.

All documents cited herein, including the foregoing, are incorporated herein by reference in their entireties for all purposes.

SUMMARY OF THE INVENTION

It is an object of this invention to obtain an implantable medical device having relatively high strength retention during the early periods of bone healing, but with a sufficiently high absorption rate so that the material is at least substantially absorbed at the time that the bone is fully healed. Preferably the device will be contourable before use (e.g., its shape can be modified to more closely complement the shape of the bone to which it will be attached) and preferably it will provide a closer match of mechanical properties of bone as compared to known devices.

To that end, a novel material has been invented which contains poly-(L-lactide/D-lactide/glycolide) also referred to hereinafter as p-(LLA/DLA/GA). This material provides mechanical properties which are desirable for certain implantable medical devices such as bone fixation devices.

In sum, the present invention relates to material comprising poly-(L-lactide/D-lactide/glycolide), preferably comprising at least about 2 molar percent D-lactide and more preferably comprising at least about 4 molar percent D-lactide. The material may have about 2 to about 10 molar percent D-lactide and/or about 80–90 molar percent L-lactide and/or about 5–15 molar percent glycolide. Espically preferred is a material comprising about 83–87 molar percent L-lactide, about 3–7 molar percent D-lactide, and about 8–12 molar percent glycolide. The material may further comprise about 0.1–5 molar percent of a polymer formed from alpha-hydroxy-alpha-ethylbutyric acid; alpha-hydroxy-beta-methylvaleric acid; alpha-hydroxyacetic acid; alpha-hydroxybutyric acid; alpha-hydroxycaproic acid; alpha-hydroxydecanoic acid; alpha-hydroxyheptanoic acid; alpha-hydroxyisobutyric acid; alpha-hydroxyisocaproic acid; alpha-hydroxyisovaleric acid; alpha-hydroxymyristic acid; alpha-hydroxyoctanoic acid; alpha-hydroxystearic acid; alpha-hydroxyvaleric acid; beta-butyrolactone; beta-propiolactide; gamma-butyrolactone; pivalolactone; or tetramethylglycolide; or combinations thereof.

The invention also relates to a process of making a material, and the material so made, the process comprising: a) combining L-lactic acid monomer, glycolic acid monomer and at least about 2 molar percent D-lactic acid monomer to form a mixture; and b) polymerizing substantially all of the mixture. The polymerization may be preformed in the presence of a catalyst and for between 24 and 72 hours.

The invention also relates to an implantable medical device comprising poly-(L-lactide/D-lactide/glycolide). The medical device may be a bone plate, bone screw, mesh, suture anchor, tack, pin or intramedullary rod. The medical device can consist essentially of unreinforced poly-(L-lactide/D-lactide/glycolide) or reinforced poly-(L-lactide/D-lactide/glycolide).

The invention also relates to a method of using a bioabsorbable bone fixation device, the method comprising: a) providing a bioabsorbable bone fixation device comprising poly-(L-lactide/D-lactide/glycolide), the device disposed in a first shape in a free state; then b) heating the bone fixation device; and then c) applying force to the device so that the device obtains a second shape in a free state which is different than the first shape and which approaches the shape of a bone surface to which it will be attached. The heating may be preformed at between about 55° C. to about 130° C. for between about 2 to about 10 seconds.

The invention also relates to polymeric resin having a heat of fusion of about 0.4–10, preferably 0.5–5J/G, and/or a molded polymeric material having a heat of fusion of about 15 to about 25 J/G, and tensile strength retention at 26 weeks of incubation of at least about 50%, and tensile strength retention at 52 weeks of incubation of at most about 25%. The polymeric material may comprise poly-(L-lactide/D-lactide/glycolide) preferably comprising at least about 2 molar percent D-lactide.

The present invention also relates to a polymeric material having tensile strength at 0 weeks of incubation of about 65–101 MPa, tensile strength at 26 weeks of incubation of about 50–75 MPa, tensile strength at 44 weeks of incubation of about 0–37 MPa, and tensile strength at 60 weeks of incubation of 0 MPa. The polymeric material may comprise poly-(L-lactide/D-lactide/glycolide) and may had a heat of fusion of about 15–25 J/G preferably about 18–21 J/G. The polymeric material may have a tensile strength at 0 weeks of incubation of about 74–92 MPa, tensile strength at 26 weeks of incubation of about 56–69 MPa, and tensile strength at 44 weeks of incubation of about 9–27 MPa.

BRIEF DESCRIPTION OF THE DRAWINGS

The following figures are provided to illustrate, but not limit, the present invention:

FIG. 1 graphically compares tensile strength as a function of incubation time of a first sample of the present invention to PLA, p-(LLA/DLA), and p-(DLA/GA);

FIG. 2 graphically compares maximum fiber strength as a function of incubation time of a second sample of the present invention to PLA, p-(LLA/DLA), and p-(DLA/GA);

FIG. 3 graphically compares inherent viscosity as a function of incubation time of a third sample of the present invention to p-(DLA/GA);

FIG. 4 graphically compares the heat of fusion as a function of percent lactide of a fourth sample of the present invention to p-(LLA/GA) and p-(DLA/GA);

FIG. 5 graphically illustrates additional embodiments of the present invention in terms of tensile strength as a function of incubation time;

DETAILED DESCRIPTION OF THE PREFERRED EMBODIMENTS

Figure 6A:
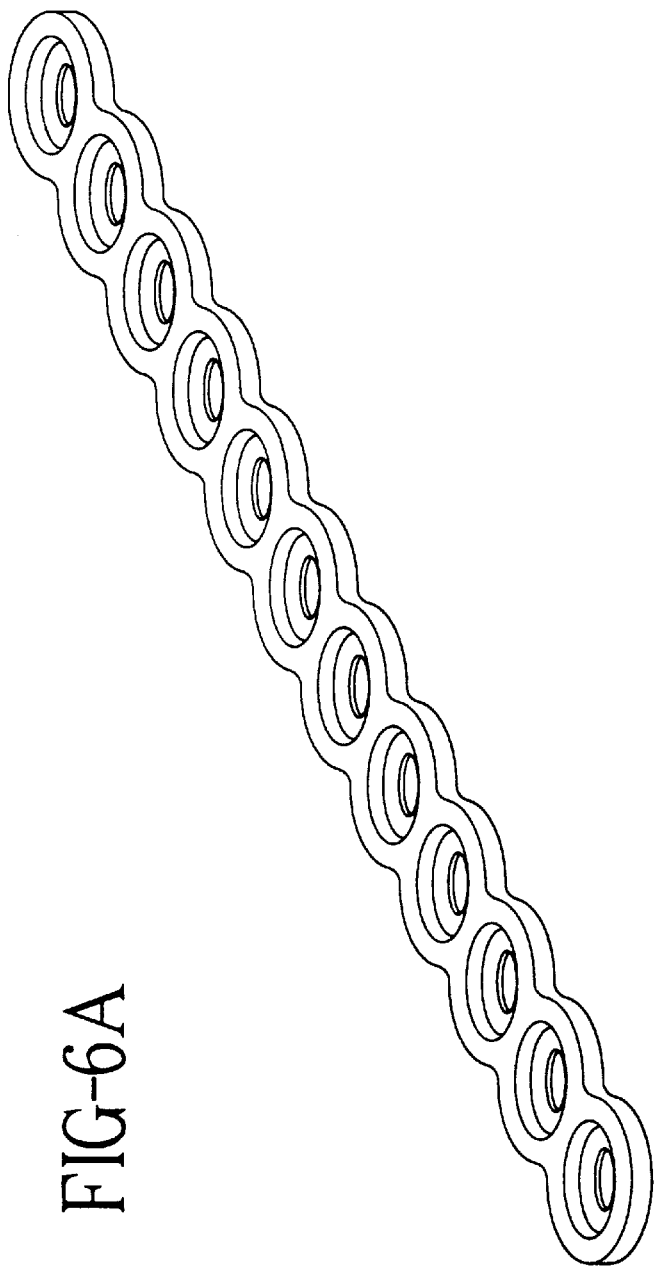
FIGS. 6(a) et seq., 7, 8, and 9 illustrate certain devices which can be made of the material of the present invention.

A bioabsorbable polymer was made having 85 molar percent L-lactide, 5 molar percent D-lactide, and 10 molar percent glycolide. The polymer was a terpolymer having repeating units of L-lactide, D-lactide and glycolide. As used herein, molar percentage of polymeric material is defined as the molar amount of a component's repeating units per molar amount of total repeating units (therefore excluding unreacted monomer and other non-polymeric materials). The terpolymer as obtained was non-reinforced and not blended or otherwise combined with other polymers. The polymer is depicted by the following chemical formula:

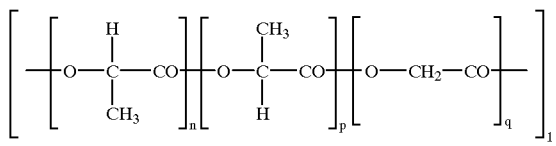

where n=0.85, p=0.05, and q=0.10.

The polymer of the present invention is preferably a terpolymer of L-lactide, D-lactide, and glycolide. However, additional compatible polymeric repeating units may be included in the materials of the present invention. Such polymeric repeating units, which will preferably be included in amounts of less than about 5 molar percent, more preferably less than about 2.5 molar percent, can be made by including the following monomers in the reactants, alone or in combination:

alpha-hydroxy-alpha-ethylbutyric acid;
alpha-hydroxy-beta-methylvaleric acid;
alpha-hydroxyacetic acid;
alpha-hydroxybutyric acid;
alpha-hydroxycaproic acid;
alpha-hydroxydecanoic acid;
alpha-hydroxyheptanoic acid;
alpha-hydroxyisobutyric acid;
alpha-hydroxyisocaproic acid;
alpha-hydroxyisovaleric acid;
alpha-hydroxymyristic acid;
alpha-hydroxyoctanoic acid;
alpha-hydroxystearic acid;
alpha-hydroxyvaleric acid;
beta-butyrolactone;
beta-propiolactide;
gamma-butyrolactone;
pivalolactone; and
tetramethylglycolide.

The polymers of the present invention will preferably have a low unreacted monomer content. Generally, the presence of monomer increases the rate of degradation of the polymer. The solid polymer will preferably contain less than about 1.0 weight percent unreacted monomers, more preferably less than about 0.3 weight percent.

Although pure poly-(L-lactide/D-lactide/glycolide) is preferred for most applications, the terpolymer can be blended with additional materials such as poly-L-lactide, poly-D-lactide, polyglycolide, poly-(L-lactide/D-lactide), poly-(D-lactide/glycolide), or polymers made from the monomers listed above. Such blending could be obtained by co-extruding the terpolymer with the additional polymeric material or by blending the polymeric materials prior to extrusion. The resulting blended material will preferably have less than 5.0 weight percent of the additional polymeric material.

The invention will preferably be a terpolymer of p-(LLA/DLA/GA) with the following specifications:

| Characteristic | Specification |
| --- | --- |
| Appearance | Granular, free of foreign contaminants |
| Color | Light tan |
| Odor | Odorless or nearly odorless |
| Co-Monomers, D&L-lactide | 88–91 mole % |
| Co-Monomer, glycolide | 9–12 mole % |
| Inherent Viscosity | 5.0–6.5 dl/g (c = 0.1 g/dl in chloroform at 25° C., capillary viscosity method) |
| Specific Rotation | >−130° in 10 cm cuvet, 0.6 g/100 ml. in Chloroform; λ = 589 nm |
| Melting Range of resin | 110–150° C. (onset-peak, 10° C./min, Differential scanning calorimeter (DSC)) |
| Heat of Fusion | 12–30 J/g |
| Water Content | <0.6% |
| Tin | Max. 50 ppm by Sulphated Ash Method |
| Heavy Metals (excluding Tin) | <10 ppm |
| Residual Monomer | Max. 0.3% |
| Residual Solvent (total) | Max. 0.1% by Head Space, Gas Chromatography method (G.C.) |

The intrinsic viscosity (I.V.) of the materials of the present invention is preferably between about 4.0 and 7.5 dl/g, more preferably between about 6.0 and 6.5 dl/g. The glass transition temperature may be approximately 60° C., and the melting point may be approximately 133° C. Samples of medical devices made of the material of the present invention have been found to have a Young's modulus of approximately 4,000 MPa and a flexural modulus of about 4,800 MPa.

Alternative embodiments of the present invention include the following terpolymers:

| | LLA Molar % | DLA Molar % | GA Molar % |
| --- | --- | --- | --- |
| (1) | 88 | 2 | 10 |
| (2) | 80 | 10 | 10 |
| (3) | 80 | 5 | 15 |
| (4) | 85 | 10 | 5 |
| (5) | 90 | 5 | 5 |

The polymers of the present invention may be made by known processes. For instance, they may be made by ring opening polymerization by charging L-lactic acid, glycolic acid, and D-lactic acid in molar percentages of 85/10/5. As used herein, molar percentage of monomers is defined as the molar amount of a monomer per molar amount of the resulting polymer. A desired amount of catalyst is also included (such as stannous octoate or zinc oxide). The reactants may be charged into a reactor under dry conditions, such as under a flow of dry nitrogen in a glovebox. The reactor is then evacuated for 15 minutes at extremely low pressures, such as 0.02 millimeters of mercury. The reactor is then refilled with dry nitrogen, and the evacuation is repeated twice. After the reactor is evacuated for the third time, it is sealed. The polymerization is then carried out in a controlled temperature oil bath at temperatures suitably between 110° C.–165° C. while the contents of the reactor are stirred. As the polymerization proceeds, the viscosity of the reaction product increases until the point is reached that the stirrer can no longer be turned. At this point, the stirrer is then shut off and the reaction is continued. Generally, the reaction time, in order to produce a polymer of the present invention, is between 24 and 72 hours. After the reaction is completed, the solid polymer is removed from the reaction vessel, cut into strips or chunks, ground, purified, and then molded or extruded to shape.

The polymers of the present invention can be produced by several commercial polymer manufacturers, such as Purac Biochem B.V., Gorinchen, the Netherlands.

EXAMPLE 1

STRENGTH RETENTION

The following four polymers were synthesized by ring opening polymerization:

(1) Homopolymer of 100 molar percent poly-L-lactide (also referred to as PLA and L);

(2) Copolymer of poly-(L-lactide/D-lactide) in a 50/50 molar ratio (also referred to as p-(LLA/DLA)and L/D);

(3) Copolymer of poly-(D-lactide/glycolide) in a 82/18 molar ratio (also referred to as p-(DLA/GA) and D/G); and (4) Terpolymer of poly-(L-lactide/D-lactide /glycolide) in a 85/5/10 molar ratio (also referred to as p-(LLA/DLA/GA) and L/D/G).

All four polymers were converted into ASTM test specimens by injection molding. These ASTM specimens were incubated in phosphate buffered saline (PBS) solution, which was maintained at pH 7.4 and 37° C. throughout the experiment period. At 0, 4, 8, 12, 26, and 52 weeks of incubation 6–10 samples of each material were taken out of the incubation vessel, tested immediately according to ASTM Method No. D638M-93 for tensile strength, and the resulting values were averaged. The averaged values are shown in Table 1 and in Figure 1.

TABLE 1

Tensile Strength as a Function of Incubation Time

Tensile Strengths, Mega Pasquals (MPa)

| Weeks of Incubation | Homo-polymer PLA | Copolymer p-(LLA/DLA) | Copolymer p-(DLA/GA) | Terpolymer p-(LLA/DLA/GA) |
|---|---|---|---|---|
| 0 | 72.7 ± 1.07 | 61.3 ± 1.84 | 82.0 ± 0.67 | 83.0 ± 2.36 |
| 4 | 67.0 ± 1.28 | 45.4 ± 1.70 | 64.5 ± 1.15 | 68.1 ± 1.28 |
| 8 | 64.7 ± 0.50 | 46.2 ± 0.88 | 65.4 ± 1.63 | 67.9 ± 0.87 |
| 12 | 64.1 ± 1.6 | 45.4 ± 1.28 | 65.8 ± 1.81 | 69.8 ± 1.26 |
| 26 | 60.0 ± 4.5 | 43.1 ± 1.72 | 3.6 ± 1.85 | 62.5 ± 1.63 |

This data illustrates that the terpolymer had improved tensile strength retention as compared to either of the copolymers. The terpolymer also had relatively fast absorption after 26 weeks as compared to the homopolymer.

EXAMPLE 2

BENDING STRENGTH

ASTM bending samples were prepared from the four polymers discussed in Example 1 by the same process as used in Example 1. The specimens were incubated in phosphate Buffered Saline (PBS) Solution, which was maintained at Ph 7.4 and 37° C. throughout the experiment period. At 0, 4, 8, 12, 26, and 52 weeks of incubation 6–10 samples of each material were taken out of the incubation vessel, tested immediately according to ASTM Method No. D638 M-93 for maximum fiber strengths, and the resulting values were averaged. The averaged values are shown in Table 2 and FIG. 2.

TABLE 2

BENDING STRENGTH AS A FUNCTION OF INCUBATION TIME

Bending Strength, Mega Pasquals (MPA)

| Weeks of Incuba-tion | Homopolymer PLA | Copolymer p-(LLA/DLA) | Copolymer (p-(DLA/GA)) | Terpolymer (p-(LLA/DLA/GA)) |
|---|---|---|---|---|
| 0 | 126.4 ± 1.69 | 113.9 ± 0.9 | 129.4 ± 1.5 | 140.8 ± 4.3 |
| 4 | 118.9 ± 2.7 | 86.4 ± 2.72 | 132.8 ± 8.1 | 123.2 ± 3.9 |
| 8 | 117.5 ± 1.9 | 92.3 ± 2.18 | 92.0 ± 11.3 | 127.2 ± 1.3 |
| 12 | 114.4 ± 2.1 | 103.7 ± 3.64 | 15.31 ± 8.1 | 122.3 ± 6.3 |
| 26 | 92.5 ± 14.26 | 97.9 ± 4.34 | 0 | 98.6 ± 9.2 |

This data illustrates that the terpolymer retains its bending strength for a greater period of time as compared to the p-(DLA/GA) copolymer. The present invention will preferably have a bending strength (Mpa) of at least 120 at 0 weeks incubation, at least 110 at 4 weeks of incubation, at least 110 at 8 weeks of incubation, at least 70 at 12 weeks of incubation, and at least 45 at 26 weeks incubation.

EXAMPLE 3

INHERENT VISCOSITY TESTS

Specimens were prepared for the terpolymer (also referred to as (p-(LLA/DLA/GA) and L/D/G)) and the copolymer (also referred to as (p-(DLA/GA))) of Example 1 by the same process as used in Example 1. Inherent viscosities of the tensile specimens were determined by the capilary viscosity method as 0.001 g/ml solution of the polymer in chloroform in a thermostated bath at 25±0.01° C. Results are given in Table 3 below and in FIG. 3.

TABLE 3

INHERENT VISCOSITY inherent Viscosity, deciliter/gram (dl/g)

| Weeks of Incubation | Copolymer (p-(DLA/GA)) | Terpolymer (p-(LLA/DLA/GA)) |
|---|---|---|
| 0 | 3.67 ± 0.17 | 4.44 ± 0.05 |
| 4 | 2.75 ± 0.16 | 3.76 ± 0.23 |
| 8 | 2.00 ± 0.39 | 3.24 ± 0.08 |
| 12 | 1.43 ± 0.08 | 2.65 ± 0.06 |
| 26 | 0.28 ± 0.11 | 1.19 ± 0.11 |
| 52 | 0.10 ± 0.01 | 0.14 |

This data indicates that the rate of loss of inherent viscosity of the terpolymer is somewhat slower than the copolymer. Therefore it is expected that the terpolymer would retain its strength for a longer period of time than the copolymer.

The present invention will preferably have an inherent viscosity (dl/g) of at least 4 at 0 weeks incubation, at least 3.2 at 4 weeks incubation, at least 2.6 at 8 weeks incubation, at least 2.0 at 12 weeks incubation, and at least 0.5 at 26 weeks incubation.

EXAMPLE 4

HEAT OF FUSION TESTS

The heat of fusion of polymers generally correlates to their crystallinity. Crystallinity of the polymer defines how easily the polymeric device will be contoured at temperatures below its melting point but above its glass transition temperature. High crystallinity in a polymer results in a lesser amount of contourability. Contouring of the bioabsorbable devices in the operating room is desirable to make the device, such as a bone plate or mesh, conform the surface of the bone so that the bone fracture can be reduced without leaving a gap between the two fragments of the bone. Therefore it is desirable to increase the ease at which a plate can be contoured.

Several resin specimens were prepared by ring opening polymerization. The heat of fusion of the specimens was determined by differential scanning calorimetry, and the results are listed in the following Table 4 and plotted in FIG. 4.

TABLE 4

HEAT OF FUSION AS A FUNCTION OF POLYMER COMPOSITION

| % Lactide in the Polymer | $\Delta H_f$, J/gm (Joules/gram) L/G | $\Delta H_f$, J/gm (Joules/gram) L/D/G | $\Delta H_f$, J/gm (Joules/gram) D/G |
| --- | --- | --- | --- |
| 100 | 67.9 | not determined | not determined |
| 95 | 50.1 | not determined | not determined |
| 90 | 43.2 | 19.5 | not determined |
| 82 | not determined | not determined | 26.8 |
| 80 | 24.8 | not determined | not determined |

This data shows that as the percent lactide in the L or D form decrease, the Heat of Fusion, $\Delta H_f$ of the polymer decreases. Furthermore, by replacing as much as 82% of the L-lactide with D-lactide in the polymer the same slope as L-lactide/glycolide polymer trend continues. However by copolymerizing only 5% D-lactide in forming a terpolymer of poly-(L-lactide/D-lactide/glycolide) in 85/5/10 molar ratio lowers the $\Delta H_f$ substantially.

Thus, the addition of poly-glycolide into the polymer, while decreasing the crystallinity of the copolymer, also decreases the strength retention of the polymer. Unexpectedly, however, the introduction of poly-D-lactide can reduce the crystallinity by an amount more than one would get by introducing mere glycolide monomer, but without a corresponding reduction of strength.

Once molded, the polymeric terpolymer of the present invention will generally have a heat of fusion of about 0.4–10 J/G, preferably 0.5–5 J/G.

FIG. 5 graphically depicts alternative embodiments of a polymeric material of the present invention defined as the shaded area between a low-end curve and a high-end curve. The coordinates of the range are as follows:

| Tensile Strength (MPA) | Weeks of Incubation |
| --- | --- |
| 101–65 | 0 |
| 90–60 | 10 |
| 80–55 | 20 |
| 75–50 | 26 |
| 70–40 | 30 |
| 50–10 | 40 |
| 40–0 | 44 |
| 25–0 | 50 |
| 0 | 60 |

Preferably the range of tensile strength would be as follows:

| Tensile Strength (MPA) | Weeks of Incubation |
| --- | --- |
| 92–74 | 0 |
| 83–67 | 10 |
| 72–61 | 20 |
| 69–56 | 26 |
| 63–47 | 30 |
| 40–20 | 40 |
| 30–10 | 44 |
| 19–0 | 50 |
| 0 | 60 |

In general, the tensile strengths can be made relatively low by including relatively large amounts of PGA, by injection molding at high temperatures (e.g. 250° C.) and/or by gamma sterilizing. Conversely, the tensile strengths can be made relatively high by including relatively small amounts of PGA, by injection molding at low temperatures (e.g. 210° C.) and/or by sterilizing with ethylene oxide sterilization methods.

Figure 6B:
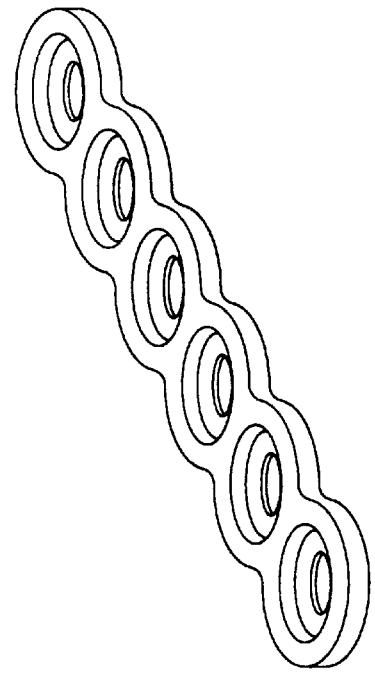
Figure 6D:
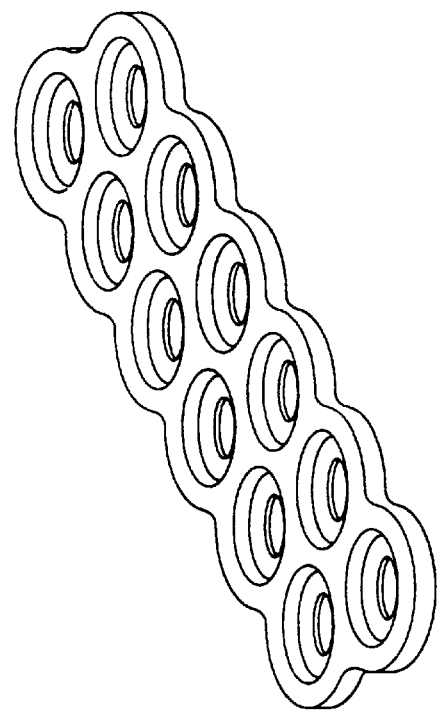
Figure 6C:
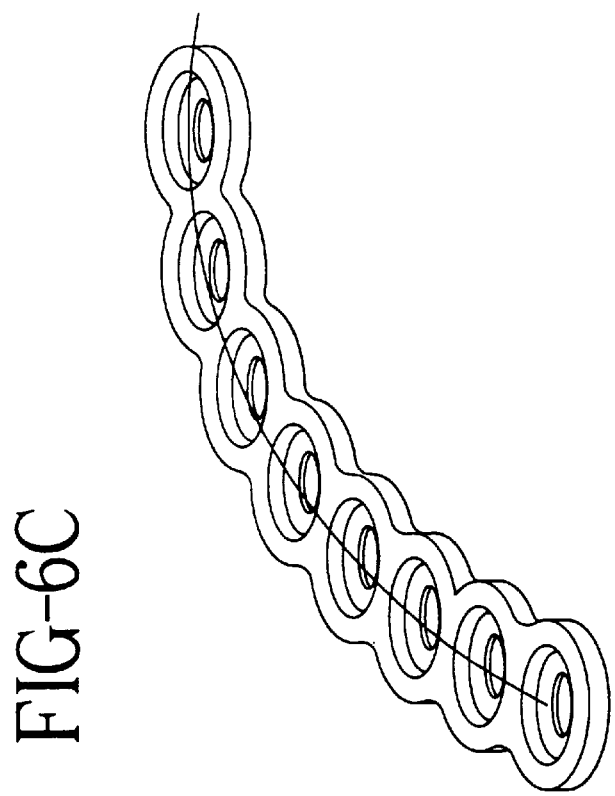
Figure 6E:
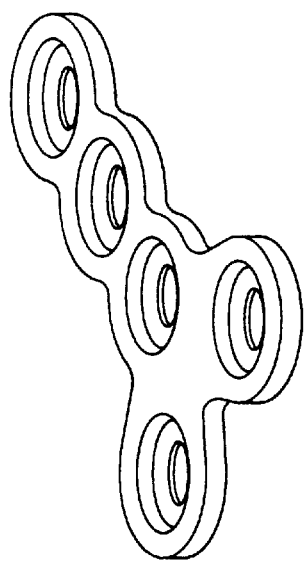
Figure 6F:
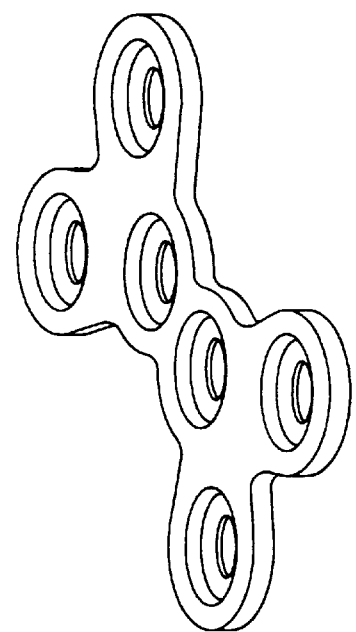
Figure 6H:
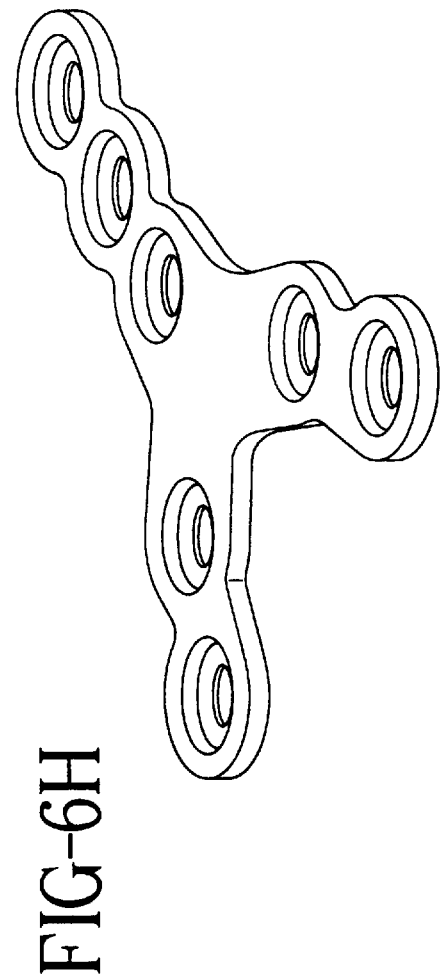
Figure 6G:
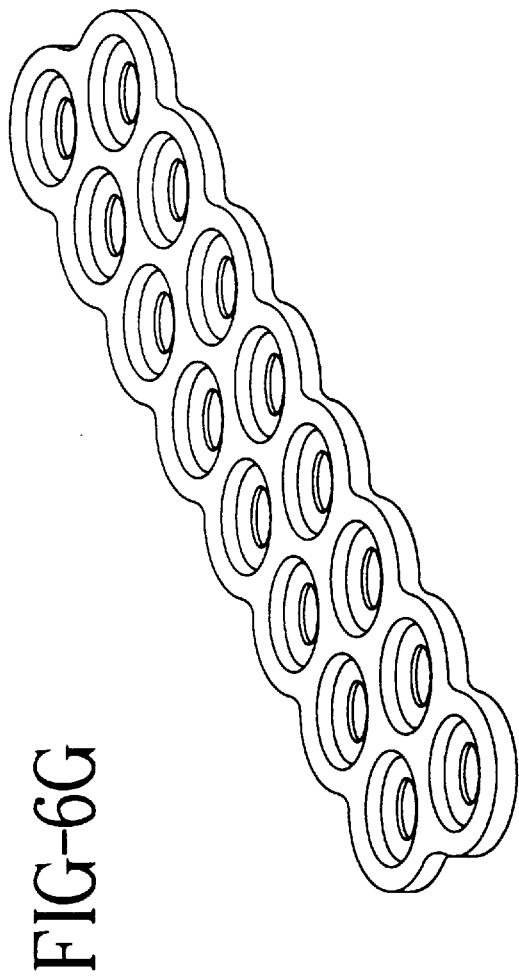
Figure 6I:
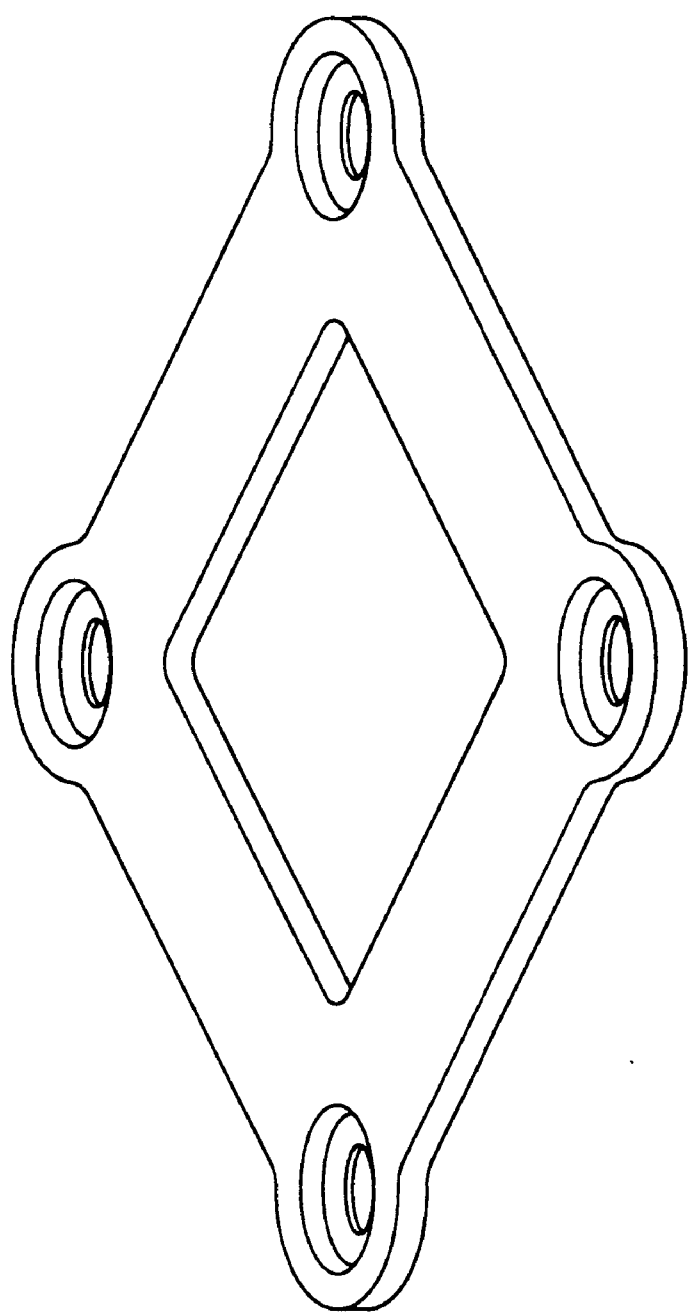
Figure 6K:
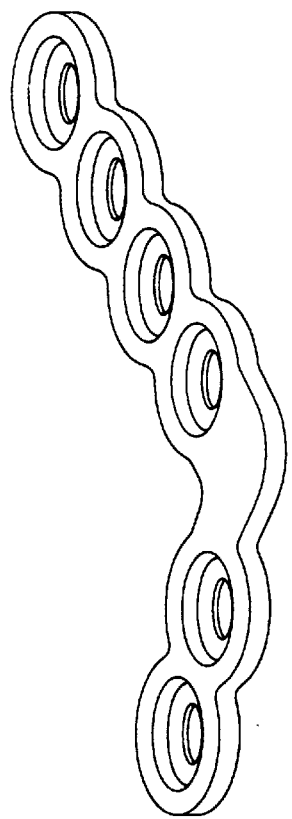
Figure 6J:
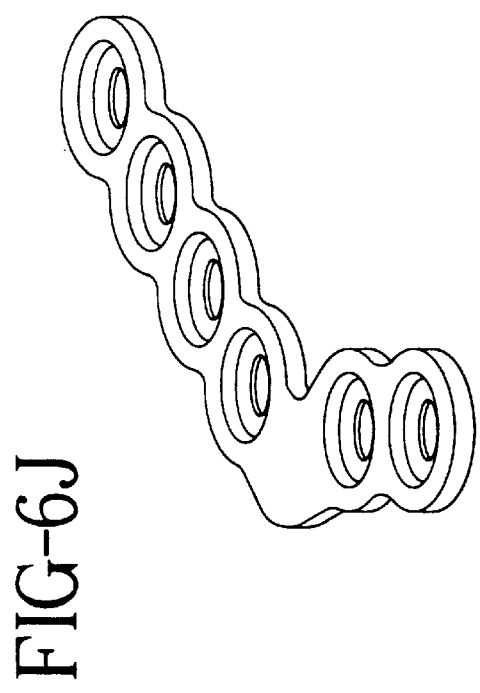
Figure 7:
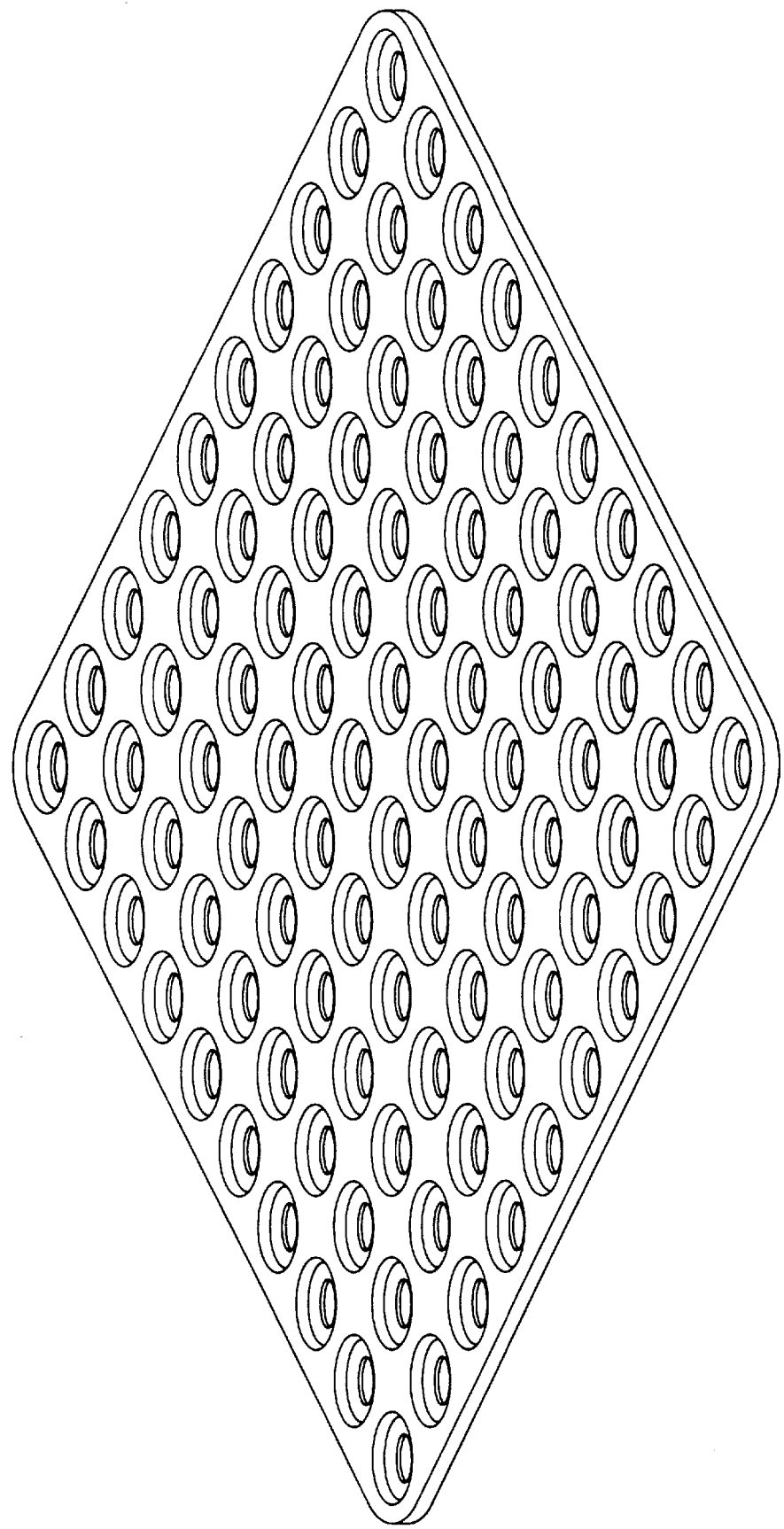
Figure 8:
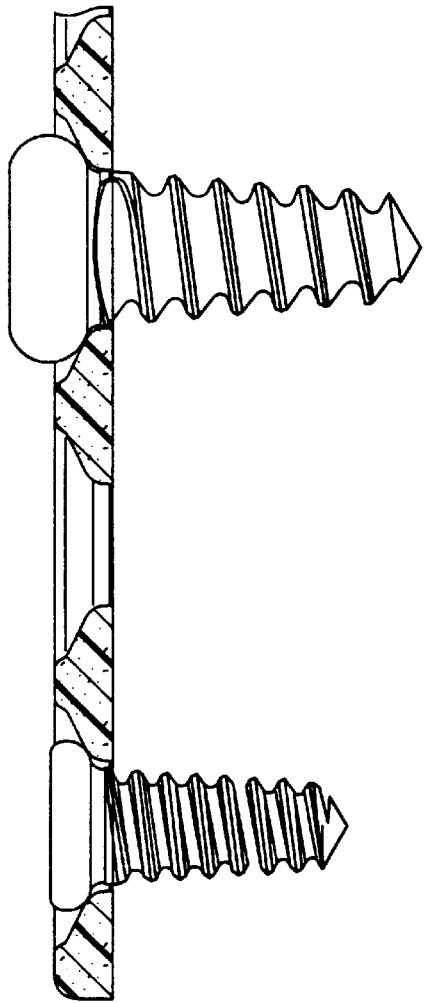
Figure 9:
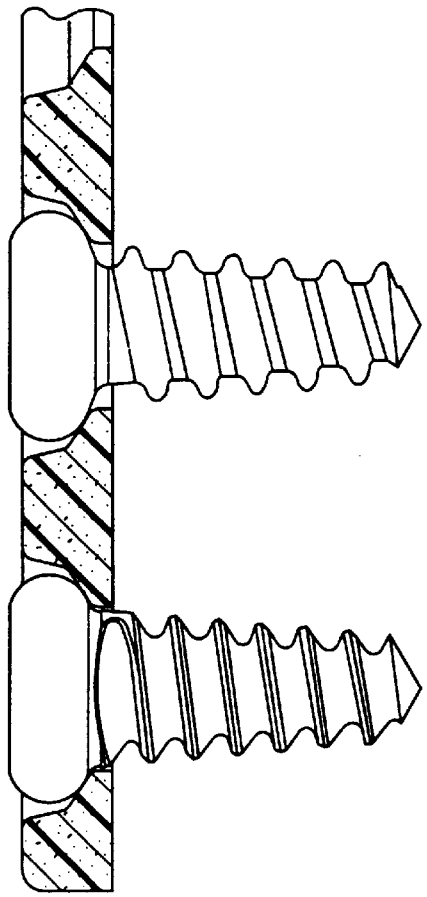

FIGS. 6(a) et seq. illustrate certain bone fixation devices which can be made of the material of the present inventions. FIGS. 6(a) illustrates a 12-hole straight plate having suitable dimensions of length 75 mm, width 7.0 mm, thickness 1.5 mm, and hole to hole spacing 6.2 mm. Alternative dimensions include width 5.5 mm, thickness 0.9 mm, and hole to hole spacing 4.5 mm. FIG. 6(b) illustrates a 6-hole straight plate. FIG. 6(c) illustrates an 8-hole curved plate. FIG. 6(d) illustrates a 12-hole ladder plate. FIG. 6(e) illustrates a 5-hole Y-plate. FIG. 6(f) illustrates an X-plate. FIG. 6(g) illustrates a 16-hole ladder plate. FIG. 6(h) illustrates a 7-hole Y-plate. FIG. 6(I) illustrates a square plate. FIGS. 6(J) and 6(k) illustrate L-plates (100 degree). FIG. 7 illustrates a 10×10 mesh which can be, e.g., 1.0 or 2.0 mm thick. FIGS. 8 and 9 illustrate profiles of screws in plates. Screws may include 1.5 mm, 2.0 mm and, 2.5 mm tapered self tapping screws.

Figure 10:
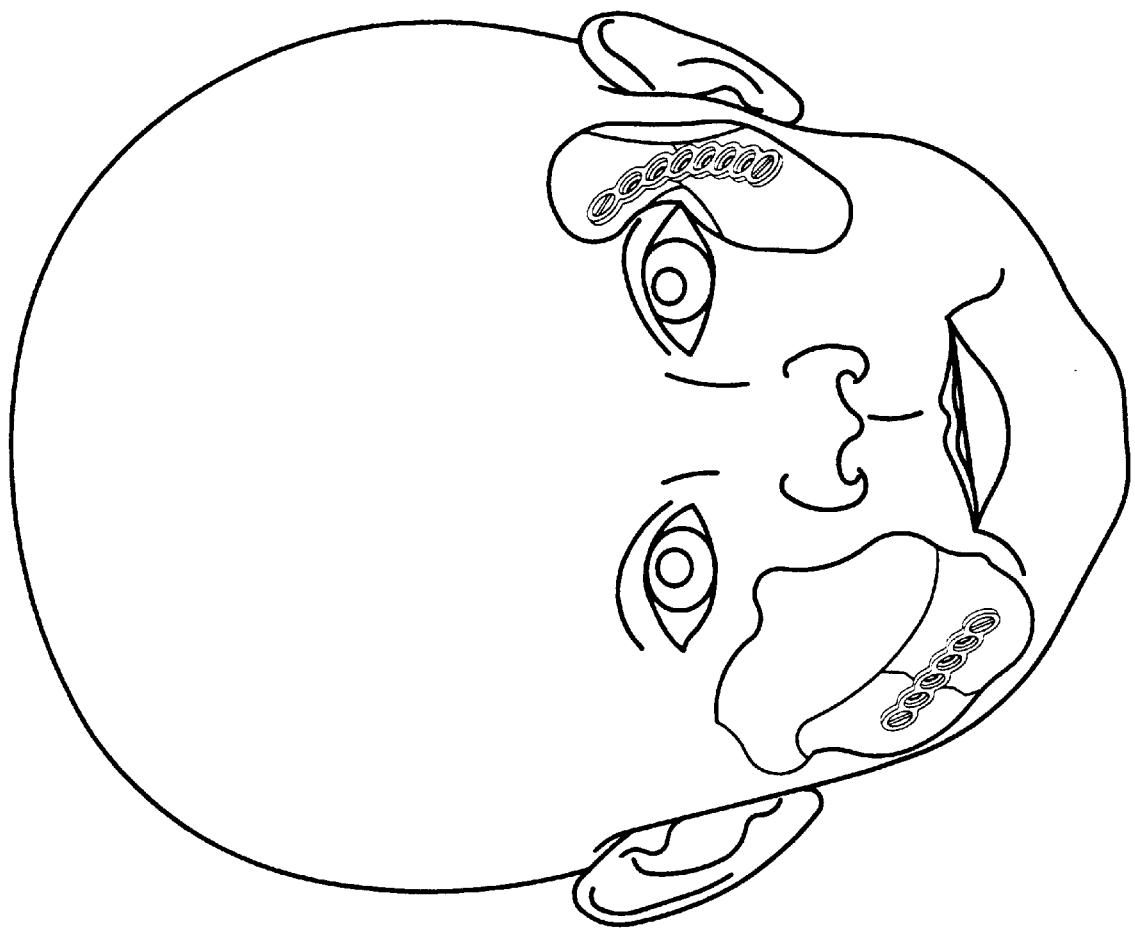
FIG. 10 illustrates bone fixation devices of the present invention attached to bone fragments.

FIG. 10 illustrates bone fixation devices, in this case an eight-hole curved plate as illustrated in FIG. 6c attached to bone around an orbit and a six-hole straight plate as illustrated in FIG. 6(b) attached to mandibular bone segments. To implant, an incision is made and soft tissue is separated exposing the bone. The device may be contoured (described below). The device is then placed across the fracture, holes are drilled, and then screws are inserted to hold the bone plate against the bone.

Figure 11:
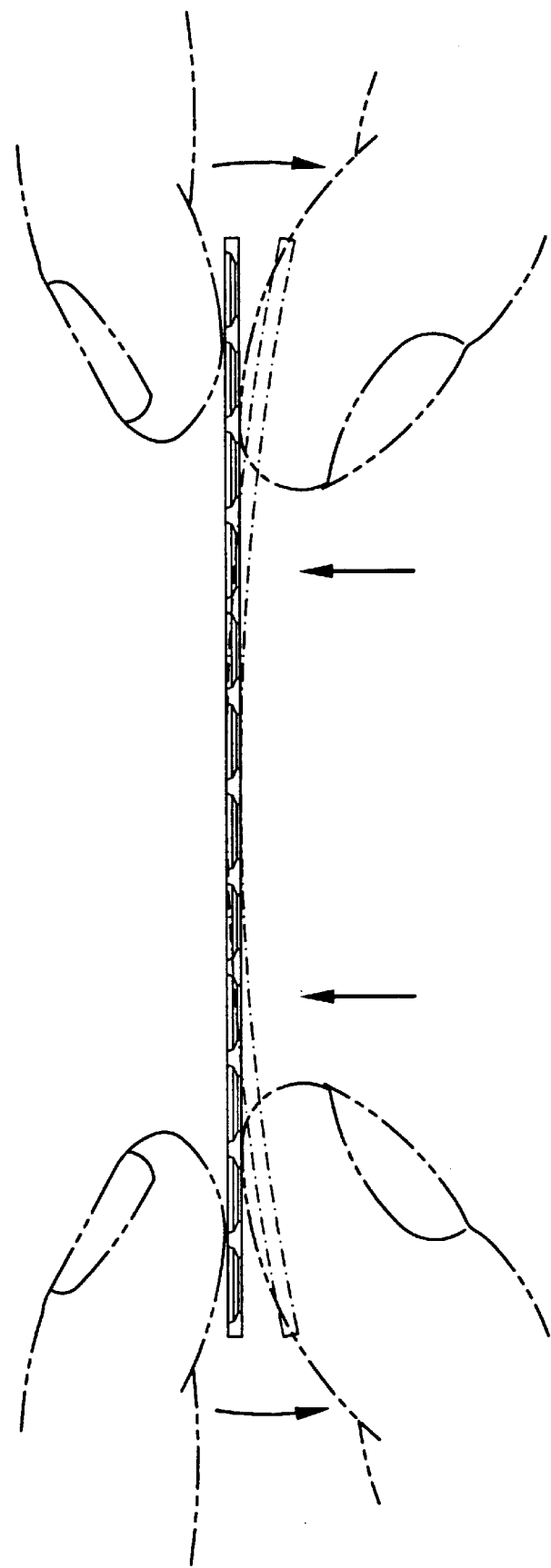
FIG. 11 illustrates a method of contouring a bone fixation device of the present invention.

FIG. 11 illustrates a method of contouring a device of the present invention. In this case, a bone fixation device (of the type illustrated in FIG. 6a) has an original flat shape depicted in solid line. This original shape is maintained in a free state, i.e., where no force is applied to the device. However, the device may be contoured by heating it to a temperature between its glass transition temperature and its melting point, e.g., between 55° C. and 130° C., preferably about 70° C., and then applying forces to the device. The arrows indicate approximate points where force can be applied after heating, such as by a doctor's fingers and thumbs in an operating room. Alternatively, after heating the device, it could be pushed against the bone fracture to be fixed in order to take its contour. Heating of the device can be done with hot water, hot air, infrared radiation, or by other heat sources, and the device is typically heated for about 2–10 seconds. The dotted lines indicate the post-contoured curved shape which would be maintained in a free state. Such a curved shape would complement the shape of certain bone segments to allow for better fixation and less gaps between the bone segments to be attached.

The foregoing figures, embodiments, and examples have been presented for purposes of illustration and not for limitation. Alternative embodiments will become apparent to one skilled in the art. For instance, in addition to the aforementioned polymers, the present invention may include additional materials such as colorants, fillers, pharmaceutical agents, and/or radiopacifying agents. In certain embodiments the material may be reinforced with a different material (polymeric or inorganic), although a non-reinforced material is preferred for most applications. The material may also be used for sutures, suture anchors, tacks, pins, plates, intramedullary rods of the upper extremity, and other implantable devices. Other uses include devices where environmental degradation would be advantageous such as fishing line, fishing nets, and in agricultural devices such as seed strips.

What is claimed is:

1. An implantable medical device comprising a terpolymer having repeating units of L-lactide, D-lactide and glycolide.

2. The medical device of claim 1 wherein the device is selected from the group consisting of a bone plate, bone screw, mesh, suture anchor, tack, pin or intramedullary rod.

3. The medical device of claim 2 consisting essentially of unreinforced poly-(L-lactide/D-lactide/glycolide).

4. The medical device of claim 3 consisting essentially of reinforced poly-(L-lactide/D-lactide/glycolide).

5. The medical device as set forth in claim 1 comprising at least about 2 molar percent D-lactide.

6. The medical device as set forth in claim 5 comprising at least about 4 molar percent D-lactide.

7. The medical device as set forth in claim 6 comprising about 2 to about 10 molar percent D-lactide.

8. The medical device as set forth in claim 7 comprising about 80–90 molar percent L-lactide, about 2–10 molar percent D-lactide, and about 5"15 molar percent glycolide.

9. The medical device as set forth in claim 8 comprising about 83–87 molar percent L-lactide, about 3–7 percent D-lactide, and about 8–12 molar percent glycolide.

10. The medical device as set forth in claim 9 consisting essentially of 85 molar percent L-lactide, 5 molar percent D-lactide, and 10 molar percent glycolide.

11. The medical device as set forth in claim 1 further comprising about 0.1–5 molar percent of a polymer formed from alpha-hydroxy-alpha-ethylbutyric acid; alpha-hydroxy-beta-methylvaleric acid; alpha-hydroxyacetic acid; alpha-hydroxybutyric acid; alpha-hydroxycaproic acid; alpha-hydroxydecanoic acid; alpha-hydroxyheptanoic acid; alpha-hydroxyisobutyric acid; alpha-hydroxyisocaproic acid; alpha-hydroxyisovaleric acid; alpha-hydroxymyristic acid; alpha-hydroxyoctanoic acid; alpha-hydroxystearic acid; alpha-hydroxyvaleric acid; beta-butyrolactone; beta-propiolactide; gamma-butyrolactone; pivalolactone; or tetramethylglycolide; or combinations thereof.

12. The medical device as set forth in claims 1 made by the process comprising:
   a) combining L-lactic acid monomer, glycolic acid monomer and at least about 2 molar percent D-lactic acid monomer to form a mixture; and
   b) polymerizing substantially all of the mixture.

13. The process of clam 12 wherein the polymerization is performed is performed in the presence of a catalyst.

14. The process of claim 13 wherein the polymerization is performed for between 24 and 72 hours.

15. The medical device as set forth in claim 1 wherein the polymer has a heat of fusion of about 0.4–10 J/G, tensile strength retention at 52 weeks at incubation of a most about 25%.

16. The medical device as set forth in claim 1 wherein the polymer has a tensile strength at 0 weeks of incubation in buffered saline at 37° C. of about 65–101 MPa, tensile strength at 26 weeks of incubation of about 50–75 MPa, and tensile strength at 52 weeks of incubation of 0 MPa.

17. The polymeric material of claim 16 having a heat of fusion of about 0.4–10 J/G.

18. The polymeric material of claim 17 having a heat of fusion of about 0.5–5 J/G.

19. The polymeric material of claim 18 formed from a resin having a heat of fusion of about 15–25 J/G.

20. The polymeric material of claim 19 formed from a resin having a heat of fusion of about 18–21 J/G.

21. The polymeric material of claim 20 having tensile strength at 0 weeks of incubation in buffered saline at 37° C. of about 74–92 MPa, tensile strength at 26 weeks of incubation of about 56–69 MPa, and tensile strength at 52 weeks of incubation of about 0 MPa.

22. The medical device as set forth in claim 1 wherein the polymer has a bending strength of at least 120 MPa at 0 weeks incubation in buffered saline at 37° C., at least 110 at 4 weeks incubation, at least 110 at 8 weeks incubation, at least 70 at 12 weeks incubation and at least 45 at 26 weeks incubation.

23. The medical device as set forth in claim 1 wherein the polymer has an inherent viscosity between about 4.0 and 7.5 dl/g.

24. The medical device as set forth in claim 23 wherein the polymer has an inherent viscosity of between about 6.0 and 6.5 dl/g.

25. An implantable medical device comprising a polymer having repeating units depicted by the formula:

$$\left[\left[O-\underset{\underset{CH_3}{|}}{\overset{\overset{H}{|}}{C}}-CO\right]_n\left[O-\underset{\underset{H}{|}}{\overset{\overset{CH_3}{|}}{C}}-CO\right]_p\left[O-CH_2-CO\right]_q\right]_l$$

where the molar percentages of the repeating units are:

$80 \leq n \leq 90$ $2 \leq p \leq 10$ $5 \leq q \leq 15$.

26. The medical devices as set forth in claim 25 wherein the polymer further comprises about 0.1–5 molar percent of a polymer formed from alpha-hydroxy-alpha-ethylbutyric acid; alpha-hydroxy-beta-methylvaleric acid; alpha-hydroxyacetic acid; alpha-hydroxybutyric acid; alpha-hydroxycaproic acid; alpha-hydroxydecanoic acid; alpha-hydroxyheptanoic acid; alpha-hydroxyisobutyric acid; alpha-hydroxyisocaproic acid; alpha-hydroxyisovaleric acid; alpha-hydroxymyristic acid; alpha-hydroxyoctanoic acid; alpha-hydroxystearic acid; alpha-hydroxyvaleric acid; beta-butyrolactone; beta-propiolactide; gamma-butyrolactone; pivalolactone; or tetramethylglycolide; or combinations thereof.

27. The medical device as set forth in claim 25 comprising at least about 4 molar percent D-lactide.

28. The medical device as set forth in claim 25 comprising about 83–87 molar percent L-lactide, about 3–7 percent D-lactide, and about 8–12 molar percent glycolide.

29. The medical device as set forth in claim 28 consisting essentially of 85 molar percent L-lactide, 5 molar percent D-lactide, and 10 molar percent glycolide.

30. The medical device as set forth in claim 25 wherein the polymer has a tensile strength of at 0 weeks of incubation in buffered saline at 37° C. of about 65–101 MPa, tensile strength at 26 weeks of incubation of about 50–75 MPa and tensile strength at 52 weeks of incubation at 0 MPa.

31. The medical device as set forth in claim 25 wherein the polymer has a bending strength of at least 120 MPa at 0 weeks incubation in buffered saline at 37° C., at least 110 at 4 weeks, at least 110 at 8 weeks, at least 70 at 12 weeks and at least 45 at 26 weeks incubation.

* * * * *

UNITED STATES PATENT AND TRADEMARK OFFICE
CERTIFICATE OF CORRECTION

PATENT NO. : 6,206,883 B1
DATED : March 27, 2001
INVENTOR(S) : Tunc

It is certified that error appears in the above-identified patent and that said Letters Patent is hereby corrected as shown below:

Column 9,
Line 53, "5"15" should read -- 5-15 --.

Column 10,
Line 12, cancel "is performed".
Line 17, "a" should read -- at --.

Signed and Sealed this

Eleventh Day of December, 2001

Attest:

NICHOLAS P. GODICI
*Attesting Officer*   *Acting Director of the United States Patent and Trademark Office*